United States Patent [19]

Yonsel et al.

[11] Patent Number: 5,527,958
[45] Date of Patent: Jun. 18, 1996

[54] PROCESS OF THE ISOLATION OF L-LEUCINE AND L-ISOLEUCINE FROM AQUEOUS SOLUTIONS

[75] Inventors: Sems Yonsel, Istinye-Istanbul, Turkey; Wiltrud Schäffer-Treffenfeldt, Obertshausen, Germany; Gérard Richet, Saint-Quentin; Tien Le Quang, Ham, both of France; Elfriede Sextl, Gieselbach; Mario Scholz, Hanau, both of Germany

[73] Assignee: Degussa Aktiengesellschaft, Frankfurt am Main, Germany

[21] Appl. No.: 309,780

[22] Filed: Sep. 21, 1994

[30] Foreign Application Priority Data

Sep. 24, 1993 [DE] Germany ............... 43 32 464.9

[51] Int. Cl.$^6$ ............................... C07C 229/08
[52] U.S. Cl. ............................... 562/554; 562/575
[58] Field of Search ............................... 562/575, 554

[56] References Cited

U.S. PATENT DOCUMENTS 4,910,336  3/1990  Goodman ............................... 562/443
5,312,980  5/1994  Yonsel et al. ............................... 562/554

FOREIGN PATENT DOCUMENTS 0571742  12/1993  European Pat. Off. .

OTHER PUBLICATIONS

Patent Abstracts of Japan, vol. 013, No. 056 (C–566) re JP-A-63 246 354, Oct. 13, 1988.
Derwent Publications Ltd., Week 9340, AN 93–317422, re JP-A-05 229 995, Sep. 7, 1993.

*Primary Examiner*—Paul F. Shaver
*Assistant Examiner*—Rosalynd A. Williams
*Attorney, Agent, or Firm*—Cushman Darby & Cushman

[57] ABSTRACT

A process for the isolation of L-leucine and L-isoleucine from an aqueous solution containing these amino acids and their separation from each other by contacting the solution with a zeolite under acid conditions.

7 Claims, No Drawings

PROCESS OF THE ISOLATION OF L-LEUCINE AND L-ISOLEUCINE FROM AQUEOUS SOLUTIONS

The present invention relates to a process for the isolation of L-leucine and L-isoleucine from aqueous solutions and the separation of the amino acids from each other.

BACKGROUND OF THE INVENTION

Leucine and isoleucine are amino acids which differ in the arrangement of the CH groups in the neutral residue.

Further properties may be found in the following table:

|  | L-leucine | L-isoleucine |
| --- | --- | --- |
| Molecular weight [g/mol] | 131.17 | 131.17 |
| Iso-electric point | pH5.98 | pH5.94 |
| Solubility [g/100 ml] | 2.19 | 4.12 |

Mixtures containing both of these amino acids are found, for example, in protein hydrolyzates. As is known from the prior art, there are considerable difficulties in separating L-isoleucine from other branched amino acids, such as L-leucine or L-valine (Ullmann, vol. A2, p. 70, 5th edition, 1985).

Proposed solutions have included, for example, fractionated crystallization of hydrochlorides (Japanese patent JP 39-1915 (1964)) or conversion of these amino acids into their cobalt salt and selective extraction of the corresponding L-isoleucine salt with alcohols from the solid phase (Japanese patent JP 37-15118 (1962), cited in H. Samejima *The Microbial Production of amino acids*, Tokyo 1972, p. 245 & p. 253).

While it is indeed known from German patent application P 42 17203.9 (European patent application 93 105321.9) that it is possible to isolate amino acids from aqueous solutions using zeolites, there is no indication of the separation of the closely related amino acids L-leucine and L-isoleucine from each other.

SUMMARY OF THE INVENTION

The object of the present invention is to provide a simple process for the separation of these two amino acids.

These and other objects are achieved, in accordance with the present invention, by a process for the isolation of L-leucine and L-isoleucine from aqueous solutions containing these amino acids and their separation from each other, in which the aqueous solutions are, optionally repeatedly, brought into contact at a pH of <7 with a zeolite having a modulus of 2 to 1000, in particular a modulus of 2 to 200, the zeolite is separated on completion of adsorption and the adsorbed amino acids, the major part of which comprises L-leucine, is desorbed with an aqueous solution adjusted to a pH of >7.

Adsorption preferably proceeds at a pH range between 1.0 and <7.0, preferably between 1 and 6. The pH of the solutions is adjusted with, for example, hydrochloric acid or sulfuric acid.

In a solution containing a mixture of leucine and isoleucine, or further neutral amino acids, the adsorption loading of leucine is higher than that of isoleucine. The remaining solution thus has a correspondingly increased concentration of isoleucine, while the leucine is adsorbed onto the solid and may readily be isolated.

Desorption is performed by exposing the zeolite to an alkaline solution, such as for example an aqueous ammonia solution. Desorption proceeds within the alkaline range of pH >7, preferably at pH 8 to 11.

Depending upon the selected pH, the desorption solution generally contains in excess of 90% of the adsorbed quantity of leucine.

By means of repeated adsorption and desorption cycles, or pH optimization during adsorption and desorption, leucine and isoleucine may be separated in such a manner that it is only leucine which is present in the alkaline desorption solution and isoleucine in the acidic parent solution.

The process proceeds in a temperature range between 15° and 60° C., without the kinetics being substantially temperature dependent. In general, the concentration of the amino acids in the solution ranges up to their respective solubility limits. However, solutions containing from 10 to 16 g/l of L-leucine and 4 to 7 g/l of L-isoleucine are of particular significance. Hydrolyzates obtained from natural sources such as pig bristle, horn or the like always contain more L-leucine than L-isoleucine (Ullmann, 5th edition, Amino Acids, vol. A2, p. 57).

The zeolites used are preferably of types A, X, in particular Y, DAY, mordenite, dealuminated mordenite, ZSM-5, dealuminated ZSM-5, Beta, VPI-5. ZSM-5 in the H or Na form with a modulus of 2 to 100 is particularly suitable (modulus refers to the molar ratio of $SiO_2$ to $Al_2O_3$). Depending upon requirements, the zeolites may be used in powder or shaped form.

DETAILED DESCRIPTION OF PREFERRED EMBODIMENT

The invention is illustrated by the following examples:

EXAMPLE 1

Use of Various Types of Zeolites

The following types of zeolites in powder form were used, wherein the calcination conditions are not of an exclusive nature.

|  |  |  | Calcination | |
| --- | --- | --- | --- | --- |
|  | $SiO_2/Al_2O_3$ | Si/Al | [°C.] | [h] |
| Mordenite | 30 | 15 | 550 | 1 |
| H-ZSM-5 | 45 | 23 | 550 | 1 |
| DAY | 200 | 100 | 950 | 1 |

A synthetic solution containing 15.2 g/l of L-leucine and 6.5 g/l of L-isoleucine was prepared and approximately 30 ml of this solution were brought into contact with approximately 3 g of zeolite powder in a 100 ml flask. The pH value was adjusted to pH 1 with HCl and the flask was shaken for approximately 20 hours at 21° C. On completion of adsorption, the supernatant was filtered and analyzed.

Zeolite loading is determined from analysis of the amino acid concentrations before ($c_o$) and after ($c_f$) adsorption and knowing the adsorbent concentration ($c_z$)=g of zeolite/amino acid solution:

$$x = \frac{C_o - C_f}{C_z}$$

The following adsorption loadings were achieved:

| Zeolite | $X_{L\text{-leucine}}$ [%] | $X_{L\text{-isoleucine}}$ [%] |
|---|---|---|
| H-ZSM-5/M45 | 4.2 | 0.32 |
| Mordenite | 2.28 | 0.97 |
| DAY | 1.92 | 0.86 |

EXAMPLE 2

Separation of L-leucine and L-isoleucine with H-ZSM-5 (M28)

The adsorption experiments were performed in shaken flasks with the zeolite in powder form. The zeolite used in this case, H-ZSM-5, has a modulus (ratio of $SiO_2/Al_2O_3$) of 28 and was calcined at 550° C. for 1 hour.

An amino acid solution containing 15.6 g/l of L-leucine and 6.6 g/l of L-isoleucine was prepared. 89.5 ml of this solution were brought into contact with 30.98 g of zeolite H-ZSM-5, modulus 28, in powder form in a 300 ml flask and the pH value was adjusted to pH 2.5 with HCl. The flask was shaken at 21° C. overnight (approximately 20 hours), the supernatant was filtered and analyzed by HPLC. After adsorption, 0.3 g/l of L-leucine and 5.7 g/l of L-isoleucine were present in the supernatant.

Before adsorption, the 89.5 ml of solution contained a total of 1.99 g of amino acids, 30% of which was L-isoleucine and 70% L-leucine. After adsorption, a total of 0.54 g of amino acids remained in the solution. Of this amount, L-isoleucine comprises 95% and L-leucine only 5%. The proportion of L-isoleucine on the zeolite was 5% (at 0.07 g) and that of L-leucine 95% (at 1.35 g).

EXAMPLE 3

Separation of L-leucine and L-isoleucine from a Mixture of Further Neutral Amino Acids 400 ml of a solution contained, in addition to 5.68 g of leucine and 3.44 g of isoleucine, further amino acids (methionine, valine, alanine, glycine, phenylalanine) in a total quantity of 10%, relative to the total quantity of amino acids.

This solution was passed through a column containing 40.54 g of zeolite pellets (H-ZSM-5, modulus 45). The pH value was adjusted to pH 1 with HCl. The experiment ran for approximately 20 hours at room temperature. After adsorption, 5.2 g of leucine and 3.24 g of isoleucine were present in the supernatant. 0.48 g of leucine and 0.2 g of isoleucine had thus been adsorbed onto the zeolites. Loadings were 1.2% for leucine and 0.5% for isoleucine.

The column was emptied, rinsed with water and desorbed with an aqueous ammonia solution. The pH value was corrected to pH 9.7 during desorption. After desorption, 0.44 g of leucine and 0.12 g of isoleucine were found in the solution. It was thus possible to desorb 92% of the leucine and 61% of the isoleucine from the zeolite.

EXAMPLE 4

Separation of Leucine and Isoleucine by Adsorption and Desorption

The experiments were performed in shaken flasks at room temperature with zeolites in powdered form. The zeolites used were H-ZSM-5, modulus 28 and H-ZSM-5, modulus 45.

|  | H-ZSM-5 Modulus 28 | H-ZSM-5 Modulus 45 |
|---|---|---|
| Concentration in initial solution | | |
| L-leucine | 10 g/l | 10 g/l |
| L-isoleucine | 10 g/l | 10 g/l |
| Leucine/isoleucine ratio | 1:1 | 1:1 |
| Weight of zeolite powder used | 23.9 g | 24.1 g |
| Weight of solution used | 232.5 g | 252.5 g |
| Adsorption at pH 5 | | |
| Concentration in the solution after adsorption | | |
| L-leucine | 4.6 g/l | 6.5 g/l |
| L-isoleucine | 9.2 g/l | 9.6 g/l |
| Zeolite loading with | | |
| L-leucine | 1.25 g | 0.88 g |
| L-isoleucine | 0.18 g | 0.05 g |
| Loading related to mass of zeolite | | |
| L-leucine | 5.25% | 3.65% |
| L-isoleucine | 0.78% | 0.21% |
| Leucine/Isoleucine ratio | 6.7:1 | 17.4:1 |

The laden zeolite was separated, washed repeatedly and dried. It was then used for the desorption experiments.

|  | H-ZSM-5 Modulus 28 | H-ZSM-5 Modulus 45 |
|---|---|---|
| Weight of desorption solution used ($H_2O$) | 6.54 g / 62.7 g | 6.03 g / 61.2 g |
| Desorption at pH 10 | | |
| Concentration in the desorption solution | | |
| L-leucine | 5.25 g/l | 3.65 g/l |
| L-isoleucine | 0.65 g/l | 0.20 g/l |
| Quantity desorbed | | |
| L-leucine | 0.33 g | 0.22 g |
| L-isoleucine | 0.041 g | 0.012 g |
| Quantity desorbed related to zeolites | | |
| L-leucine | 5.05% | 3.65% |
| L-isoleucine | 0.68% | 0.21% |
| Leucine/Isoleucine ratio | 7.4:1 | 17.4:1 |

The tests show that the adsorption results in a clear increase in concentration of the leucine.

While L-leucine and L-isoleucine are present in the initial solution in a quantity ratio of 1:1, after desorption, the ratio found in the desorbed liquid is 7.4:1 (modulus 28) or even 17.4:1 (modulus 45).

Presented in other terms, these results have the following significance for the purification of L-leucine using type ZSM-5/M45:

| Purity in the initial solution: | 50% |
|---|---|
| Purity after 1st separation stage | 94.5% |

| | |
|---|---|
| (adsorption + desorption): | |
| Purity after 2nd separation stage (adsorption + desorption): | 99.6% |

What is claimed is:

1. A process for the isolation of L-leucine and L-isoleucine from an aqueous solution containing these amino acids and for their separation from each other, said method comprising contacting an aqueous solution containing L-leucine and L-isoleucine with a zeolite having a modulus of 2 to 1000 at a pH of <7, separating the zeolite on completion of adsorption by the zeolite, and desorbing adsorbed amino acids from the zeolite with an aqueous solution adjusted to a pH of >7.

2. A process as set forth in claim 1 in which said aqueous solution is contacted with said zeolite repeatedly.

3. A process according to claim 1 in which adsorption is performed at a pH range between 1 and <7.0.

4. A process according to any one of claims 1–3 in which desorption is performed at a pH range between 8 and 11.

5. A process according to any one of claims 1–3 in which the zeolite is selected from the group consisting of zeolites of the types A, X, Y, DAY, mordenite, dealuminated mordenite, ZSM-5, dealuminated ZSM-5, Beta and VPI-5.

6. A process according to claim 5 in which the zeolite is ZSM-5 type in the H or Na form.

7. A process according to any one of claims 1 to 3 in which the solution contains further neutral amino acids.

* * * * *